United States Patent
Schütze et al.

(10) Patent No.: US 11,578,350 B2
(45) Date of Patent: *Feb. 14, 2023

(54) APPARATUS FOR CHARACTERIZING BIOLOGICAL OBJECTS

(71) Applicant: CellTool GmbH, Tutzing (DE)

(72) Inventors: Raimund Schütze, Tutzing (DE); Karin Schütze, Tutzing (DE)

(73) Assignee: CELLTOOL GMBH

(*) Notice: Subject to any disclaimer, the term of this patent is extended or adjusted under 35 U.S.C. 154(b) by 666 days.

This patent is subject to a terminal disclaimer.

(21) Appl. No.: 15/724,816

(22) Filed: Oct. 4, 2017

(65) Prior Publication Data

US 2018/0023111 A1 Jan. 25, 2018

Related U.S. Application Data

(62) Division of application No. 13/702,839, filed as application No. PCT/EP2011/002839 on Jun. 9, 2011, now abandoned.

(30) Foreign Application Priority Data

Jun. 9, 2010 (DE) .................... 10 2010 023 099.5

(51) Int. Cl.
*C12Q 1/04* (2006.01)
*G01N 15/14* (2006.01)
(Continued)

(52) U.S. Cl.
CPC .............. *C12Q 1/04* (2013.01); *C12Q 1/025* (2013.01); *G01N 15/1468* (2013.01);
(Continued)

(58) Field of Classification Search
CPC .... C12Q 1/025; C12Q 1/04; G01J 3/44; G01J 3/4412; G01N 15/1468; G01N 15/1484;
(Continued)

(56) References Cited

U.S. PATENT DOCUMENTS 5,694,216 A 12/1997 Riza
6,067,859 A 5/2000 Käs et al.
(Continued)

FOREIGN PATENT DOCUMENTS

DE 10352416 6/2005
DE 102004008762 9/2005
(Continued)

OTHER PUBLICATIONS

Kemper et al. (2010) J. Biophotonics 7: 425-31 (Year: 2010).*
(Continued)

*Primary Examiner* — Robert J Yamasaki
*Assistant Examiner* — Charles Zoltan Constantine
(74) *Attorney, Agent, or Firm* — Sand, Sebolt & Wernow Co., LPA

(57) ABSTRACT

In order to quantitatively characterize biological objects, for example individual cells, a stimulus is applied to a biological object (8) in a contactless fashion. A measurement and a further measurement are performed on the biological object (8) in order to ascertain a response of the biological object (8) to the stimulus, wherein the measurement and the further measurement comprise detecting Raman scattering on and/or in the biological object (8) and/or capturing data using digital holographic microinterferometry (DHMI). The biological object (8) is characterized according to a result of the measurement and is sorted if needed. The stimulus can be applied by means of a laser beam that creates optical tweezers or an optical trap, by means of ultrasonic waves or an electric or magnetic radio frequency field.

26 Claims, 9 Drawing Sheets

(51) Int. Cl.
*G01N 21/65* (2006.01)
*G01N 21/45* (2006.01)
*G03H 1/04* (2006.01)
*C12Q 1/02* (2006.01)
*G01J 3/44* (2006.01)

(52) U.S. Cl.
CPC .......... *G01N 21/453* (2013.01); *G01N 21/65* (2013.01); *G03H 1/0443* (2013.01); *G01J 3/44* (2013.01); *G01N 15/1484* (2013.01); *G01N 2015/149* (2013.01)

(58) Field of Classification Search
CPC .......... G01N 2015/149; G01N 21/453; G01N 21/65; G03H 1/0443; H04L 41/0803; H04L 41/0806; H04L 41/0893; H04L 67/141; H04L 67/146; H04L 67/30; H04L 67/34; H04L 67/42
See application file for complete search history.

(56) References Cited

U.S. PATENT DOCUMENTS

| | | | |
|---|---|---|---|
| 7,435,568 B2 | 10/2008 | Käs et al. | |
| 9,134,242 B2* | 9/2015 | Shaffer | G01B 11/002 |
| 2004/0012778 A1 | 1/2004 | Li et al. | |
| 2005/0048581 A1 | 3/2005 | Chiu et al. | |
| 2005/0084912 A1 | 4/2005 | Poponin | |
| 2005/0221333 A1 | 10/2005 | Sundararajan et al. | |
| 2005/0247866 A1 | 11/2005 | Plewa et al. | |
| 2006/0192969 A1* | 8/2006 | Marks | G01N 21/65 356/451 |
| 2009/0067018 A1* | 3/2009 | Pu | B82Y 20/00 359/1 |
| 2010/0315628 A1 | 12/2010 | Mertsching et al. | |
| 2011/0165558 A1 | 7/2011 | Popp et al. | |

FOREIGN PATENT DOCUMENTS

| | | |
|---|---|---|
| DE | 102005036326 | 2/2007 |
| DE | 102005044422 | 3/2007 |
| DE | 102006045618 | 5/2008 |
| EP | 1059871 | 12/2000 |
| EP | 1631788 | 3/2006 |
| WO | 2005112042 | 11/2005 |
| WO | 2006130728 | 12/2006 |
| WO | 2007014622 | 2/2007 |
| WO | 2007141539 | 12/2007 |

OTHER PUBLICATIONS

Schaal (2009) J. Eur Optical Society Rapid Publication Jun. 3, 2009 p. 09028-1 to 09028-5 (Year: 2009).*
Rao et al. (2009) J. Raman Spectrosc. 40: 1257-61 (Year: 2009).*
StellarNet ("What is a Flow Cell?" Stellar Net, Feb. 26, 2017, Tampa, Florida, available at www.stellarnet.us/what-is-a-flow-cell, accessed on Jul. 23, 2021) (Year: 2017).*
F. Schaal et al.: "Marker-Free Cell Discrimination by Holographic Optical Tweezers," Journal of the European Optical Society, Jun. 3, 2009.
Börn Kemper et al.: "Monitoring of Laser Micromanipulated Optically Trapped Cells by Digital Holographic Microscopy," Journal of Biophotonics, vol. 3, No. 7, Jun. 8, 2010.
Satish Rao et al.: "Polarization Raman Study of Protein Ordering By Controllable RBC Deformation," Journal of Raman Spectroscopy, vol. 40, No. 9, Sep. 1, 2009.
S. Rao et al.: "Raman Study of Mechanically Induced Oxygenation State Transition of Red Blood Cells Using Optical Tweezers," Biophysical Journal, vol. 96, No. 1, Jan. 7, 2009.
Mehdi Daneshpanah et al.: "3D Holographic Imaging and Trapping for Non-Invasive Cell Identification and Tracking," Journal of Display Technology, IEEE Service Center, New York, NY, US, vol. 6, No. 10, Oct. 1, 2010.
Nelson Cardenas et al.: "Probing Orientation and Rotation of Red Blood Cells in Optical Tweezers by Digital Holographic Microscopy," Proceedings of SPIE, Jan. 1, 2011.
Nelson Cardenas et al.: "Stretching of Red Blood Cells by Optical Tweezers Quantified by Digital Holographic Microscopy," Proceedings of SPIE, Jan. 1, 2011.
Kember B et al.: "Modular Digital Holographic Microscopy System For Marker Free Quantitative Phase Contrast Imaging of Living Cells," Proceedings of SPIE, The International Society for Optical Engineering Spie, USA, vol. 6191, Jan. 1, 2006.
Gajendra P. Singh et al.: "Real-Time Detection of Hyperosmotic Stress Response in Optically Trapped Single Yeast Cells Using Raman Microspectroscopy," Analytical Chemistry, vol. 77, No. 8, Apr. 1, 2005.
K Svoboda et al.: "Biological Applications of Optical Forces," Annual Review of Biophysics and Biomolecular Structure, vol. 23, No. 1, Jun. 1, 1994.
M. Radmacher et al., "Measuring the Viscoelastic Properties of Human Platelets With The Atomic Force Microscope," Biophys. J. 70, 556 (1996).
Kemper B. et al.: "Investigation of Living Pancreas Tumor Cells by Digital Holographic Microscopy," Journal of Biomedical Optics 11(3), 034005 (May/Jun. 2006).
Constable A. et al.: "Demonstration of a Fiber-Optical Light-Force Trap," Optics Letters, vol. 18, No. 21, Nov. 1, 1993.
Kemper B et al.: "Digital Holographic Microscopy: A Method For Marker-Free Dynamic Analysis of Living Cells," Biophotonics and Microscopy, Photonik International, 2007.
Kemper B et al.: "Integral Refractive Index Determination of Living Suspension Cells by Multifocus Digital Holographic Phase Contrast Microscopy," Journal of Biomedical Optics, Sep./Oct. 2007.
Song W.Z. et al.: "Determination of Single Living Cell's Dry/Water Mass Using Optofluidic Chip," Applied Physics Letter 91, 223902(2007).
Wang W. et al.: "Self-Aligned Dual-Beam Optical Laser Trap Using Photorefractive Phase Conjugation," Optical Society of America, vol. 14, No. 4, Apr. 1997.
Flynn R.A. et al.: "Counter-Propagating Optical Trapping System For Size and Refractive Index Measurement of Microparticles," Biosensors & Bioelectronics 21, 2006.
Kaneta T. et al.: "An 'Optical Channel': A Technique For The Evaluation of Biological Cell Elasticity," Analytical Chemistry, vol. 73, No. 24, Dec. 15, 2001.
Rappaz B. et al.: "Measurement of the Integral Refractive Index and Dynamic Cell Morphometry of Living Cells With Digital Holographic Microscopy," Optics Express, vol. 13, No. 23, Nov. 14, 2005.
Chichester J. et al.: "Cell Deformation Induced By Linear Diode Bar Optical Stretchers. I. Experiment," Optical Society of America, 2009.
Lyncée Tec SA: DHM™ T1000. "Biological Specimen 3D Morphology and Refractive Index Separation," 2006.
Lyncée Tec SA: DHM™ T1000. "Real-Time 3D Monitoring of Living Biological Specimens," 2006.

* cited by examiner

APPARATUS FOR CHARACTERIZING BIOLOGICAL OBJECTS

CROSS-REFERENCE TO RELATED APPLICATIONS

This application is a Divisional of U.S. patent application Ser. No. 13/702,839 filed Dec. 7, 2012, the entire disclosure of which is incorporated herein by reference.

U.S. patent application Ser. No. 13/702,839, filed Dec. 7, 2012, is a National Stage Entry of PCT/EP2011/002839 having an international filing date of Jun. 9, 2011, which claims priority from DE1020100239005, filed Jun. 9, 2010.

BACKGROUND OF THE INVENTION

Technical Field

The invention relates to a method and an apparatus for characterizing biological objects, for example individual cells. The invention relates in particular to a method and an apparatus which allow biological objects in a microfluidic system to be characterized in a contactless fashion and to then be sorted.

Background Information

Various techniques for observing and manipulating biological objects are known, by means of which the targeted manipulation and observation was made possible for ever smaller objects, for example individual cells. Various techniques for analyzing biological objects use a targeted stimulation of the biological objects. The manipulation of individual cells for measuring their elasticity properties using a scanning force microscope as described in M. Radmacher et al., "Measuring the Viscoelastic Properties of Human Platelets with the Atomic Force Microscope", Biophys. J. 70, 556 (1996) belongs to such techniques. Traditionally, such techniques are frequently used to gain knowledge on the structure, the functionality and the properties of biological objects.

DE 10 2005 036 326 A1 and WO 2007/014622 A1 describe a method and an apparatus for analyzing biological objects. In this case, a change in shape or volume of a biological object is monitored by means of digital holographic microinterferometry (DHMI). However, such measurements do not provide information on changes in the interior of the biological object.

Raman spectroscopy may be used to determine properties in the interior of a cell. For characterizing and sorting cells, one can make use of the Raman spectrum of dead cells being different from the Raman spectrum of living cells, for example. Based on the Raman spectrum, it can thus be determined whether a cell is dead or alive. Techniques in which Raman spectroscopy is performed on biological objects are conventionally limited to only one Raman spectrum being captured for a biological object. This may impede a characterization in cases in which, for example, different biological objects have similar or identical Raman spectra under the present measurement conditions.

The gentle, contactless and if possible marker-free characterization of biological objects becomes increasingly important, for example in biological research, in stem cell research, in genetic research, in medical diagnosis or in forensic sciences. Time is an important factor in such applications. For practical applications, it is important to obtain a sufficient throughput of biological objects in the characterization. If biological objects are mechanically stimulated one by one, it may be difficult to obtain a sufficient throughput. Setting a stimulus may also be performed using biochemical substances. However, this may have the effect that the biological object becomes useless for a further analysis, depending on the respective biological object of interest and the substance which is used.

For practical applications there is moreover a need to perform the characterization of biological objects with even greater accuracy. Additionally, a large degree of automation is desirable. Using conventional methods and apparatuses, an automatic recognition of the desired biological objects is frequently not possible or is possible with great effort only. This is partly due to the fact that, in conventional methods and apparatuses, only one monitoring technique is used or three-dimensional objects are represented only two-dimensionally, for example. When using conventional techniques, such as a laser scanner, a three-dimensional imaging requires a time-consuming scanning of various planes and a subsequent digital combination of the image data. This impedes a more extensive automation of the characterization of cells.

BRIEF SUMMARY OF THE INVENTION

It is an object of the invention to provide a method and an apparatus for characterizing biological objects, wherein a simple, fast and accurate characterization of individual biological objects is possible. In particular, it is an object of the invention to provide such a method and such an apparatus in which a stimulus is applied to the biological object and which is not only based on using two-dimensional images of an external change of the biological object, but which provides information on processes in an interior of the cell.

According to the invention, this object is attained by a method and an apparatus as defined in the independent claims. The dependent claims define embodiments of the invention.

According to the invention, a stimulus is applied to a biological object and a response of the biological object is measured using Raman scattering and/or digital holographic microinterferometry (DHMI) to characterize biological objects. In the art, DHMI is also known as digital holographic microscopy.

To ascertain the response of the biological object
 a DHMI measurement for determining a refractive index and/or a detection of Raman scattering is performed before application of the stimulus, and
 a further DHMI measurement for determining a refractive index and/or a further detection of Raman scattering is performed after or during application of the stimulus,
with the biological object being characterized based on a comparison of the results of the measurements.

In particular, the intrinsic response to the stimulus may be observed in the method and the apparatus. Advantageously, the response to the stimulus may be determined both with regard to extrinsic parameters, for example the shape or the volume of the object, and with regard to intrinsic parameters, for example the local molecular composition or the local refractive index within the cell. The method and the apparatus allow a more comprehensive characterization of cells. For illustration, external changes may not only be imaged in two dimensions, but in three dimensions. By means of DHMI and/or Raman spectroscopy, the intrinsic responses to the stimulus may be analyzed.

The characterization of the biological objects is made based on a comparison of the measurement results which are determined before application of the stimulus and during or after application of the stimulus. Greater flexibility in the characterization of biological objects is thereby attained. Even if different biological objects have similar Raman spectra under the given measurement conditions, for example, a change in the Raman spectrum can be detected using the method and the apparatus according to embodiments. This allows objects to be discriminated which have similar Raman spectra under certain measurement conditions, while the Raman spectra show different changes in response to application of the stimulus. For example, during application of the stimulus a shift of a Raman spectrum, of individual spectral lines or spectral weights may occur, which is characteristic for the biological object. Different biological objects may also show different return characteristics after application of the stimulus. These may be monitored as a function of time in the Raman spectrum and may be used for the characterization.

Analogously, the response of the biological object to a stimulus may be monitored using DHMI for determining a refractive index. In this case, the refractive index may be detected at plural times to monitor return characteristics of the biological object after application of the stimulus which can be used for characterization.

Biological objects may show significantly different response characteristics after application of a stimulus even when they have a similar morphology or topology and thus cannot be easily discriminated using conventional 2D images. By means of Raman scattering, the scattering characteristics of the biological object may be detected. Based on the frequency shifts of the light scattered on the biological object, a characteristic behaviour of the object, for example with regard to vibration spectra of molecules and thus with regard to the molecules which are present, can be detected. Since plural spectral lines of a vibration spectrum or of plural vibration spectra may be detected in measuring Raman scattering, a characteristic vibration spectrum may be detected after application of the stimulus to the biological object. For example, individual molecules may be identified. Chemical changes may be shown by detecting the Raman spectrum, which chemical changes are attributed to pathological cells in tumor tissue, for example. Thereby, tumor cells may be discriminated from healthy cells, for example. Raman spectra may also provide information on the differentiation stage of cells and may thereby discriminate stem cells from body cells.

Digital holographic microinterferometry (DHMI) is a holographic measurement technique. Two phase-coherent partial beams, an object beam and a reference beam, are superimposed. The resulting interference image is captured by an electronic image sensor, such as a CCD sensor. Different object planes can be reconstructed from a single DHMI image, so that additional information is available for the characterization of cells. By means of DHMI, molecular changes in an interior of the individual cells may be imaged indirectly, so that the cell types can be characterized quickly and in a contactless fashion according to their morphological properties such as layer thickness, volume, micro-movements or deformations. Due to these characteristics, dynamic processes after application of a stimulus to the biological object may be monitored by means of DHMI data acquisition and may be used for characterization of the biological object. A reliable analysis of the biological object is possible also in the presence of optical blur, for example upon movement of the object in the depth direction during data acquisition, because a focus correction may be performed automatically and with the aid of a computer. A mechanical focus correction may be omitted. This allows a very fast data acquisition without time-consuming scanning and thereby helps increasing the throughput.

In an embodiment, a DHMI data acquisition may be performed on a cell to determine a ratio of nucleus to cytoplasm. Alternatively or additionally, typical nucleus patterns may be quantified according to their different refractive characteristics. Thereby, the method and the apparatus according to embodiments of the invention may be used for cytometry.

In the methods and apparatuses, the stimulus is advantageously applied such that the biological object is not destroyed or damaged. The power irradiated onto the biological object for Raman spectroscopy and/or DHMI is set such that it does not lead to a destruction of the biological object. Thus, the biological object remains an intact biological object both before and after application of the stimulus. Both when using Raman spectroscopy and when using DHMI, characteristic properties of biological objects can be determined without a marking of the biological object being required for this purpose.

With the method according to the invention and the apparatus according to the invention, a contactless and marker-free characterization of a biological object is possible which does not destroy the biological object. In this process, biological objects may be characterized according to their response to a stimulus which is measured by Raman spectroscopy and/or DHMI.

The further Raman spectroscopy and/or the further data acquisition for DHMI for determining a refractive index is performed after the stimulus was applied or while the stimulus is being applied. In this manner, the return characteristics of a biological object, such as a cell, may be monitored after a change was induced by the stimulus. It is also possible that more than two Raman spectra are detected in a time-sequential manner to monitor the response of the biological object as a function of time.

A difference spectrum of a Raman spectrum captured in a measurement and of a further Raman spectrum captured in a further measurement may be computed. The difference spectrum may be compared to reference difference spectra which are stored in a data base to characterize the biological object.

A laser light source which is used for the Raman spectroscopy may also be used to generate a resonant vibration of the biological object. In this case, light output by the laser light source is first irradiated onto the biological object in a pulsed fashion with a repetition rate. The repetition rate may be adjusted to excite a resonance vibration of the biological object. By monitoring the 3D shape it can be controlled whether the resonance has been reached. Alternatively or additionally, reaching the resonance may be monitored based on a captured Raman spectrum. Upon reaching the resonance, the laser intensity may be reduced for example to avoid destruction of the biological object. While the biological executes resonance vibrations, changes in the interior of the biological object may be observed by means of DHMI for determining a refractive index and/or by means of Raman spectroscopy.

The measurement performed on the biological object may comprise both a Raman spectroscopy and a data acquisition by means of DHMI.

By combining Raman spectroscopy and DHMI for measuring a shape, both an external change of the biological object, such as a change in shape or volume, and a change in the interior of the biological object may be determined. The determined change in the interior which is also referred to as intrinsic change may be a change in the refractive index monitored by DHMI or a change in the scattering characteristics in the Raman spectrum in response to the stimulus. When compared to techniques which only determine changes in the shape of the object, additional information may thus be obtained which may be used for characterizing the object. Additionally, shape or volume changes after application of the stimulus to the biological object can be determined using DHMI. When a Raman spectroscopy is also performed, information on changes of the captured Raman spectrum and thus of the vibration spectrum may also be obtained. A change in the protein or molecular composition may be determined, for example. The results obtained by DHMI and Raman spectroscopy may be correlated to characterize or identify the biological object more accurately.

The stimulus may be applied in a marker-free manner. Thereby it can be ensured that the biological object is available for further study after its characterization. This is in particular advantageous when the characterization is performed for sorting living cells.

The stimulus may be applied to the biological object using optical radiation. The stimulus may be applied such that a deformation of the biological object is induced. Various techniques may be used for this purpose. According to an embodiment at least one optical tweezer or trap is generated using one or plural laser beams. In an embodiment an optical tweezer is generated using at least one laser beam which holds the biological object in a fluid flow having a finite flow velocity. In this case, the laser power and thus the depth of the trap potential and the flow velocity of the fluid flow may be set such that the shear forces applied by the fluid onto the biological object lead to a deformation of the biological object. In this manner, a deformation of the biological object may be attained by the interplay of fluid forces and optical forces. The laser beam may be directed along a fluid channel or counter the fluid channel. In this process, plural biological objects may be held simultaneously along a longitudinal direction of the fluid channel.

In embodiments, the optical tweezer which holds the object at a desired position may be constituted by the beam which is irradiated onto the object for performing the Raman spectroscopy.

According to another embodiment, a pair of optical tweezers can be used for applying the stimulus, by means of which forces may be generated on opposite sides of the biological object such that a deformation of the object is realized, for example. The two optical tweezers may be moved laterally to induce stretching of the object, for example. In another embodiment, a laser beam or a pair of essentially counter-propagating laser beams may be used, the power and profile of which are set such that forces are applied onto the biological object which compress or stretch the biological object in a propagation direction of the laser beams. In another embodiment, the cell may be deformed using a micro beam or two counter-propagating micro beams. In this process, a laser beam with which light is irradiated onto the biological object for a short time only is advantageously used as a micro beam. For example, a pulsed laser may be used to generate the micro beam. Alternatively, the beam of a continuously operating laser may be affected, for example using an electro-optical element, such that it impinges onto the biological object for a short time span as a micro beam. A local disturbance on the membrane and/or in the cytoplasm of a cell may also be induced using a micro beam, e.g. by optoperforation and optoporation, respectively. The resultant change in the protein composition may be detected using Raman spectroscopy and/or the change in the morphology and the refractive index, respectively, of the cell may be detected using DHMI.

In further embodiments, a stimulus may be applied without inducing deformation of a biological object, which stimulus comprises local heating, for example. The response thereto can be detected by DHMI and/or Raman spectroscopy.

In each one of these embodiments, the beam path of the laser beam or the laser beams, respectively, may be scanned over different positions. In this manner, stimuli may be applied to biological objects which are held at different measurement positions. A deflection device may be provided which scans the laser beam or the laser beams, respectively, in a controllable manner. In an embodiment, an optical element, e.g. a mirror, may be adjusted in a controlled manner for this purpose. In another embodiment, a laser beam may also be scanned over different positions by means of a SLM (spatial light modulator) crystal. In an embodiment, the scanning may be performed such that the laser beam or the laser beams, respectively, are directed onto different fluid channels in a time-sequential manner. Alternatively or additionally, the scanning may be performed such that the laser beam or the laser beams, respectively, are directed onto different measurement positions which are spaced along a longitudinal direction or a transverse direction of a channel to apply the stimulus to various biological objects. In an embodiment, the scanning is performed in two dimensions, with the laser beam(s) being adjusted both between different fluid channels and along the longitudinal direction of the channels between different positions at which a stimulus is to be applied to biological objects. If at least two laser beams are directed onto a biological object for applying a stimulus, the two laser beams are scanned synchronously. A parallelisation or multiplexing, respectively, in characterizing biological objects may be attained by use of the mentioned procedures, which allows the throughput to be increased further.

A data acquisition by means of DHMI may be performed after a deformation of a biological object was induced using optical methods. A data acquisition is additionally performed before applying the stimulus in order to be able to judge the response of the biological object. Thereby, cells or other biological objects and their changes may be reconstructed in three dimensions and the response to the stimulus may be quantified. Various cross sections of the biological object may be reconstructed from a single DHMI image. Upon deformation in response to an optically induced stimulus there generally results a change not only in one cross section of the biological objects, but typically a change in three dimensions. For a non-homogeneous object, such as a cell, the response to compressive or tensile forces has different degrees in the three dimensions. Using 3D imaging by means of DHMI more accurate information on the elasticity characteristics in the various directions can be obtained. Digital refocusing upon performing a computer-aided evaluation of the DHMI data allows one to forgo a mechanical focus correction. Moreover, the complete cell volume may be captured with a single snapshot in DHMI, such that scanning is not required. In this manner, the throughput in the characterization may be increased.

The refractive index of a cell or of components of the cell, such as the cell nucleus, respectively, is determined in a quantitative manner by DHMI data acquisition. Plural DHMI data acquisitions may be performed to determine the refractive index, with the cell being rotated or changed in its position between the various DHMI data acquisitions. A rotation of the cell may be induced by the laser beam or the laser beams, respectively, which are also used for applying the stimulus to the cell. A laser beam profile which is not rotationally symmetric may be used to induce a rotation of the cell. This profile may be generated by using an optical fibre having an elliptic cross section, for example. It is also possible that laser beams are used which have a helical wave front. For illustration, counter-propagating laser beams may be used which have a Laguerre-Gauss-profile and a helical wave front such that the Poynting vector varies in a spiral shape along the axis which defines the propagation direction. Such beams transfer a torque onto the biological object with which the biological object can be rotated. Alternatively or additionally, optical fibres may be used which provide radiation with which the biological object can be rotated. The optical fibres may have a cross section which is not rotationally symmetric. The fibres may have an elliptic cross section, for example.

Laser beams may also be used to hold the biological object in a solution at a desired position. When a deformation of the biological object is induced using a laser beam, an optical tweezer or optical trap for the object may also be generated by this laser beam. This allows a holographic data acquisition to be performed on an individual cell in a solution.

A Raman spectroscopy may be performed before application of a stimulus and after or during application of the stimulus. For example, the Raman spectroscopy may be performed both before application of the stimulus and after or during the stimulus is applied using optical or other techniques. In this manner, a change in the cellular activity during an induced stress may be monitored in the Raman spectrum, for example. Additionally, the deformation of the biological object may be quantitatively determined by computer-aided processing of conventional 2D images. In addition to changes in the Raman spectrum information on the degree of cross-linking of structural molecules, such as the microtubule network or the actin network can be obtained by quantitative measurement of the elasticity.

When a Raman spectroscopy is performed a measurement laser beam which is irradiated onto the biological object for the Raman spectroscopy may be scanned between different positions. A scanning may be performed along a fluid channel of a microfluidic system and/or between different fluid channels of the microfluidic system. In this manner one can attain that the average duration of a measurement process is not limited by the time scale which is required to position a new biological object such that a Raman spectroscopy can be performed thereon. A beam path for the DHMI data acquisition may also similarly be adjusted between different locations in a controlled manner. This may in particular be advantageous when the different biological objects on which measurements are to be performed in parallel have a distance which is greater than a diameter of the object wave for DHMI data acquisition in an object plane. If plural laser beams are irradiated onto the biological object for the corresponding measurement, e.g. in a Raman spectroscopy in which the light of the excitation laser for the Raman spectroscopy also generates the trap potential for the biological object, the plural laser beams are scanned synchronously.

When a Raman spectroscopy is performed in methods and apparatuses according to embodiments, it is not required that the complete Raman spectrum be detected. For example, only a part of the spectrum, e.g. individual spectral lines, may be detected. This may be sufficient for a comparison with a data base in which characteristic spectral lines of the Raman spectrum or the shift thereof in response to the stimulus are stored. The spectral range in which the Raman spectroscopy is performed may be selected as a function of the biological objects which are to be characterized.

The stimulus onto the biological object does not necessarily have to be applied using optical radiation. Rather, ultrasonic waves or electromagnetic fields, in particular high-frequency fields, may also be used. The stimulus may also be applied chemically, for example by administration of active substances or drugs. The stimulus may also be applied mechanically, for example by moving the cells over structured surfaces or by relocating cells onto surfaces.

In all embodiments, conventional microscopy may also be performed in addition to a Raman spectroscopy and/or a DHMI data acquisition. For illustration, a phase contrast microscopy, a fluorescence microscopy or another microscopy may be used to enable microscopic observation of the object which is being characterized.

Preferably, a microfluidic system is used in the embodiments of the invention. Biological objects may be kept in solution using the microfluidic system. This allows a characterization to be performed on living cells. Advantageously, the biological object to be characterized, for example a cell, is transported in the microfluidic system. For performing the measurement on the biological object, the biological object may then be brought to a desired measurement position for example by using optical tweezers or traps or a diversion pulse of a laser micro beam with which the biological object may be removed from a circulating fluid flow or by using microfluidic valves or other adjusting elements.

In the various embodiments, the Raman spectroscopy and/or DHMI data acquisition may advantageously also be performed on the object in a fluid channel. Both the measurement before application of the stimulus and the further measurement which is performed during or after application of the stimulus may be performed on the object in the fluid channel.

The microfluidic system may have a closed fluid loop in which biological objects are transported until the measurement is performed thereon. Sinking of biological objects may thereby be reduced. The sample in solution may be supplied to the characterization to a large extent.

In the methods and apparatuses according to various embodiments, it is possible that not only one stimulus is applied, but plural stimuli having various intensity and/or of various type may be applied. The response of the biological object to the various stimuli may be determined using Raman spectroscopy and/or DHMI to characterize the biological object. Accordingly, an apparatus may have plural devices which allow stimuli of different types to be applied. For example, a device for applying a stimulus using optical techniques, a device for applying a stimulus using ultrasonic waves and/or a device for applying a stimulus using high-frequency fields may be provided. In this manner, the behaviour of the object in response to different stimuli may be determined. Extrinsic and/or intrinsic changes may respectively be detected. In an embodiment, the behaviour of the cell after application of at least two different stimuli is determined using both DHMI and Raman spectroscopy, with the two different stimuli being respective applied using one of laser radiation, ultrasound or electromagnetic high-frequency fields. A deformation of a cell may give rise to a rearrangement of proteins in addition to changes in shape and volume. By using ultrasound a local molecular composition may be changed and/or heat may be generated, for example. By using electromagnetic high-frequency fields, an oscillation of molecules and thus an intrinsic change of the object may be induced. By data acquisition using DHMI and/or Raman spectroscopy a biological object may be characterized with regard to its external parameters but also with regard to processes in the interior of the object.

The characteristics of Raman spectroscopy and DHMI allow the characterization of biological objects to be automated to a large degree. In particular, the spectra obtained by Raman spectroscopy and/or the information on shape, volume and/or refractive index obtained from DHMI are suitable for a largely automatic characterization. The acquired Raman spectra and/or information on volume and shape of the biological object may be compared with a data base, for example, to automatically sort cells. In this manner, healthy cells may be discriminated from tumor cells, for example, and may be automatically directed to different collection vessels. In further embodiments, certain cells, cell cycles or clones may be recognized by evaluating the response upon application of a respective stimulus.

BRIEF DESCRIPTION OF THE SEVERAL VIEWS OF THE DRAWINGS

In the following, the invention will be explained with reference to the drawing by means of preferred embodiments.

DETAILED DESCRIPTION OF THE INVENTION

Figure 1:
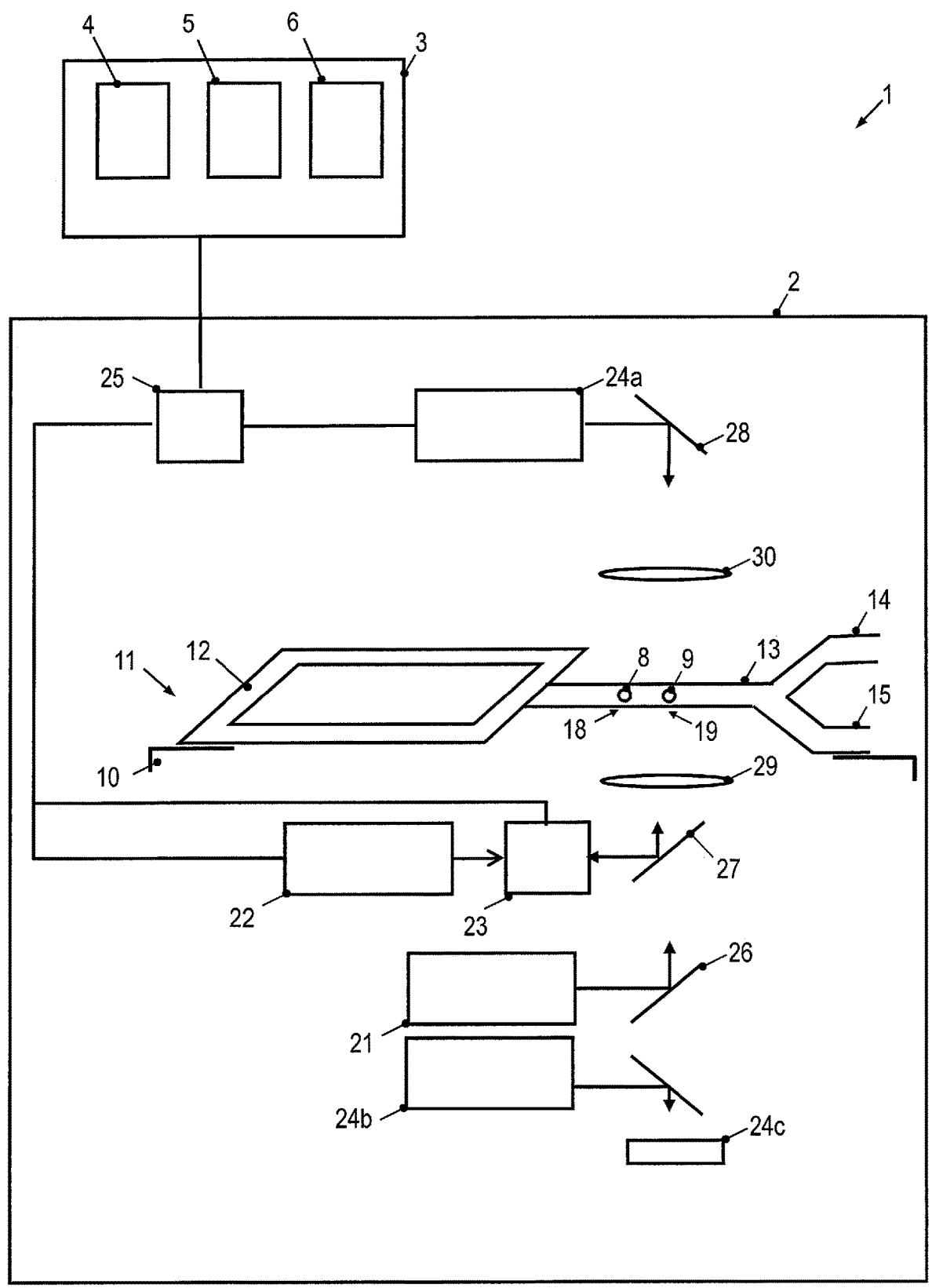
FIG. 1 shows a schematic representation of a system for characterizing and sorting biological objects according to an embodiment.

FIG. 1 is a schematic representation of a system 1 for sorting biological objects according to an embodiment. The system 1 comprises an apparatus 2 for characterizing biological objects and a computing device 3 coupled to the apparatus 2. The apparatus 2 performs a Raman spectroscopy and/or a digital holographic microinterferometry (DHMI) on a biological object to quantitatively determine its response to a stimulus. Measurement results which are acquired thereby are output to the computing device 3 via an interface. The computing device 3 has a data base 4 which has information regarding the behaviour of different biological objects. For example, the data base 4 may comprise information on a Raman spectrum after application of the stimulus, information on shifts of spectral lines of the Raman spectrum in response to the stimulus, information on shape or volume after application of the stimulus or information on changes in the shape or changes in the volume for various types of cells (healthy cells or tumor cells), for different stages of a cell cycle or similar. Depending on a comparison of the acquired and processed data, which may represent a change in a Raman spectrum or a refractive index for example, to a threshold value or a comparison of the acquired data with the data base 4, the computing device 3 may output a control command for sorting the biological object to the apparatus 2, may output information on the object over a display device 5 or may offer various options for a further processing of the object to the user which the user may select over a user interface 6.

The apparatus 2 is configured to characterize cells in a contactless manner and quickly. The apparatus 2 has a microfluidic system 11 which is supported by a carrier 10. The microfluidic system 11 comprises a closed fluid loop 12. A continuous fluid flow may be maintained in the closed fluid loop 12 during operation of the apparatus 2 using suitable microfluidic devices to prevent sedimentation of biological objects which are transported in a solution in the fluid loop 12. The characterization of cells is performed in the microfluidic system 11. This allows measurements to be performed on living cells or cell clusters. The microfluidic system 11 has a fluid channel 13. To characterize biological object, e.g. cells, the cells 8, 9 are positioned in the fluid channel 13. Although FIG. 1 exemplarily shows a separate fluid channel 13 into which the cells may be displaced from the closed fluid loop 12, for example using microfluidic devices or an optical tweezer, the fluid channel 13 may also be a portion of the closed loop 12. A laser pulse is also suitable to transport the cell from a laminar flow into a neighbouring channel where the measurement is performed.

For performing a characterization, the cell 8 is positioned in a measurement region 18 and the cell 9 is positioned in a measurement region 19. The measurement regions 18, 19 are spaced along the longitudinal axis of the fluid channel 13. The measurement regions 18, 19 may be defined by the focal area of laser beams, for example, which form an optical trap or an optical tweezer for the cells 8 and 9, respectively. A fluid flow in the fluid channel 13 may be stopped when a measurement is to be performed on the cells 8, 9. A centering in the channel may be performed by hydrodynamic focussing, for example. A positioning along the channel occurs automatically, for example upon performing a Raman spectroscopy, when the cells 8, 9 are drawn into the focal area of the laser beam which is irradiated for performing the Raman spectroscopy.

While a configuration according to an embodiment is shown in FIG. 1 in which plural measurement regions 18, 19 are spaced in a longitudinal direction of the channel in the channel 12 various other configurations may be realized in each one of the embodiments described herein. For example, the measurement may respectively be performed on an individual object only so that the parallel execution of measurements may be forgone. In another embodiment, different biological objects on which a measurement is performed may be spaced in a transverse direction of the channel. For this purpose, plural biological objects may be positioned in transversally spaced portions of a laminar flow in a channel or in plural transversally spaced laminar flows.

It is also possible that plural biological objects are positioned in channels which are transversally spaced when the measurement is performed.

The apparatus 2 has a device 21 for generating a stimulus to the cells 8, 9. The device 21 may comprise a laser source, a source for electromagnetic radiation, in particular in a high-frequency range, or a device for generating ultrasonic waves. For illustration there is shown a configuration in which the device 21 has a laser source for generating a micro beam which may be irradiated onto the cells 8 and 9 in the measurement regions 18 and 19, respectively, via a beam splitter 26 and a lens 29. A power of the laser source 21 may be set such that a local disturbance is induced on the cell membrane or/and in the cytoplasm of the cells 8, 9 by the micro beam. Other configurations of the device are also possible which allow a stimulus to be applied using a laser beam. In particular, the device 21 may be configured such that it generates a laser beam or plural laser beams having an energy density, a profile and a direction which induce a deformation of the cell 8, 9. It is also possible that two counter-propagating pulsed laser micro beams are used, with a deformation of the cell being induced by a laser pulse or a sequence of laser pulses. In this case, the two beams are pulsed such that they simultaneously provide light power to the biological object. It is also possible that an excitation beam for Raman spectroscopy is irradiated onto the biological object in a pulsed manner. A repetition rate of the pulses may be varied to excite a resonance vibration of the biological object. The occurrence of the resonance may be detected and controlled by monitoring the 3D shape, for example by DHMI. A closed loop control may be provided to adjust the laser light power upon occurrence of the resonance such that a destruction of the biological object may be prevented.

The apparatus 2 further has at least one of a device 22 for performing a Raman spectroscopy and a device 24a, 24b, 24c for performing a DHMI. With this device or these devices, respectively, the behaviour of the cell 8, 9 in response to the stimulus is determined. The apparatus 2 of the system 1 of FIG. 1 comprises both the device 22 for performing the Raman spectroscopy and a device 24a, 24b, 24c for performing DHMI. Depending on the application, only one of these devices may be present. A controllable deflection device 23 is provided to deflect an excitation beam of the device 22 for performing the Raman spectroscopy such that the spectrum of the cell 8 or of the cell 9 is selectively measured. The excitation beam of the Raman device 22 is directed via a beam splitter 27 and a lens 29, e.g. the objective of a microscope, onto the cell 8, 9. A control and evaluation logic 25 is coupled to the Raman device 22, the deflection device 23 and the DHMI device 24a, 24b, 24c to control these devices for performing a data acquisition and to evaluate the data captured by the Raman device 22 and the DHMI device 24a, 24b, 24c. The Raman device 22 and the DHMI device 24a, 24b, 24c respectively perform a data acquisition before, during or after application of the stimulus on the respective cell 8, 9 to ascertain the response of the cell to the stimulus. By comparing the DHMI and Raman signals captured before application of the stimulus and after or during application of the stimulus, information on the behaviour of the cells in response to the stimulus can be obtained.

Similarly to solids, biological objects also have vibration spectra which are dependent on cell activity and stages of a cell cycle, for example. Accordingly, changes induced by the stimulus may be monitored. For performing the Raman spectroscopy on living biological objects the Raman device 22 may comprise a diode laser having a wavelength of 785 nm, for example. The laser beam may be focussed onto the cells 8, 9. Cells and bacteria are not damaged at this wavelength. The scattered Raman signals are measured by means of a spectrometer. The spectrometer may be provided with a CCD sensor optimized for near infrared, for example.

An adjustment of the laser beam irradiated onto the cells for Raman spectroscopy using the deflection device 23 may also be performed such that the biological object, for example the cell, is sampled at plural points. Thereby, a Raman spectrum may be captured for each one of the various measurement points. Conclusions on the chemical or biochemical composition of the biological object may be drawn from the various spectra after application of the stimulus. This information may be determined with a spatial resolution by performing a scan over the biological object.

The Raman device 22 may be configured such that a position of a focus of the excitation beam may be adjusted in all three spatial directions for performing the Raman spectroscopy. When the apparatus 2 comprises an optical microscope, the Raman device 22 is advantageously configured such that the position of the focus of the excitation beam for performing the Raman spectroscopy may be controlled independently of a focus of the microscope beam path.

The detection of Raman spectra may be performed such that before or after capturing the Raman spectra on a biological object a Raman spectrum of a substrate on which the biological object is positioned is also captured. This background spectrum may be used to computationally subtract signal components which are caused by the substrate from the data acquired by Raman spectroscopy on the biological object. The position and height of peaks in the background spectrum may be compared to the position and height of peaks in the Raman spectra detected on the biological object to determine a multiplicative factor which specifies the weight of the background signal in the Raman spectra captured on the biological object and which is taken into account in the computational subtraction of the background spectrum. For example, the background spectrum may be multiplied by a multiplicative factor which specifies the weight before it is subtracted from the Raman spectra captured on the biological object. Subtraction of the background spectrum may in particular be advantageously employed when the biological object is positioned directly on a solid substrate.

The DHMI device is configured such that a laser beam is split into two partial beams, which form an object wave and a reference wave which is phase coherent thereto. The object wave and the reference wave may be directed via suitable optical components such that the object wave is directed onto the object, with signals of the object wave which are scattered or reflected on the object impinging onto a two-dimensional image sensor, such as a CCD sensor. The reference wave impinges onto the two-dimensional image sensor without being reflected or scattered on the object. In FIG. 1, the DHMI device has a component 24a which is schematically shown and which outputs the object wave. The object wave is directed via a beam splitter 28 and a condenser lens 30 onto one of the cells 8, 9 or is simultaneously directed onto both cells 8, 9. The reference wave is directed from a component 24b via a beam splitter onto a two-dimensional image sensor 24c, such as a CCD sensor. The interference pattern which results from the phase differences between the object wave and the reference wave at the image sensor 24c allows the shape of the biological object to be reconstructed.

The DHMI device having components 24a, 24b, 24c provides a contactless, marker-free and quantitative phase contrast imaging. Various object planes can be reconstructed from a single hologram captured using the DHMI device 24a, 24b, 24c. A minimally invasive dynamic detection of deformations and movements of living cells in three dimensions is also possible in addition to a marker-free analysis of topography and morphology, respectively. A digital refocusing may also be performed by computationally evaluating the signal captured by the image sensor 24c. Stability may thereby be attained even when the cell moves in a depth direction. Deformations of the biological objects may thereby be detected in three dimensions for characterizing a cell.

Using the apparatus 2 the response of a biological object may be examined both with regard to changes in the topography or morphology and with regard to changes in the Raman spectrum. The measurement of the response to a known stimulus allows the behaviour of the biological object to be captured both with regard to changes in the morphology and topography, respectively, and with regard to changes in the Raman spectrum. By comparison with a corresponding data base a determination can be made, for example, which cell type is present, in which stage of a cell cycle the cell is, etc. Both Raman spectroscopy and DHMI are fast measurement techniques which can capture the essential characteristics, i.e. the spectrum and hologram, respectively, in a single shot. In embodiments, only a part of the Raman spectrum is detected to be able to carry out a comparison with a data base. Individual lines of a Raman spectrum may be detected, for example, based on which a comparison with known data sets can be performed. In this manner a further increase of the throughput can be attained. The relevant lines may be measured once before application of the stimulus and once more during or after application of the stimulus. Differences of the spectral weights, i.e. of the peaks in the detected spectrum may be determined for the relevant lines of the spectrum to characterize the biological object based on the differences.

The biological objects may be processed further because the characterization is performed marker-free and without destruction of the biological object in the apparatus 2 of FIG. 1. To this end, a signal may be provided by the control and evaluation logic 25 or by the computing device 3 according to which the cell 8, 9 is selectively sorted into one of plural output channels 14, 15 of the microfluidic system 11.

The block diagram representation of the various components of the apparatus 2 is to be regarded as being a schematic representation. For illustration, components of the Raman device 22, 23 may also be provided such that the excitation beam is coupled in via the lens 30. Alternative configurations of the device 21 with which the stimulus is applied are also possible.

Figure 2:
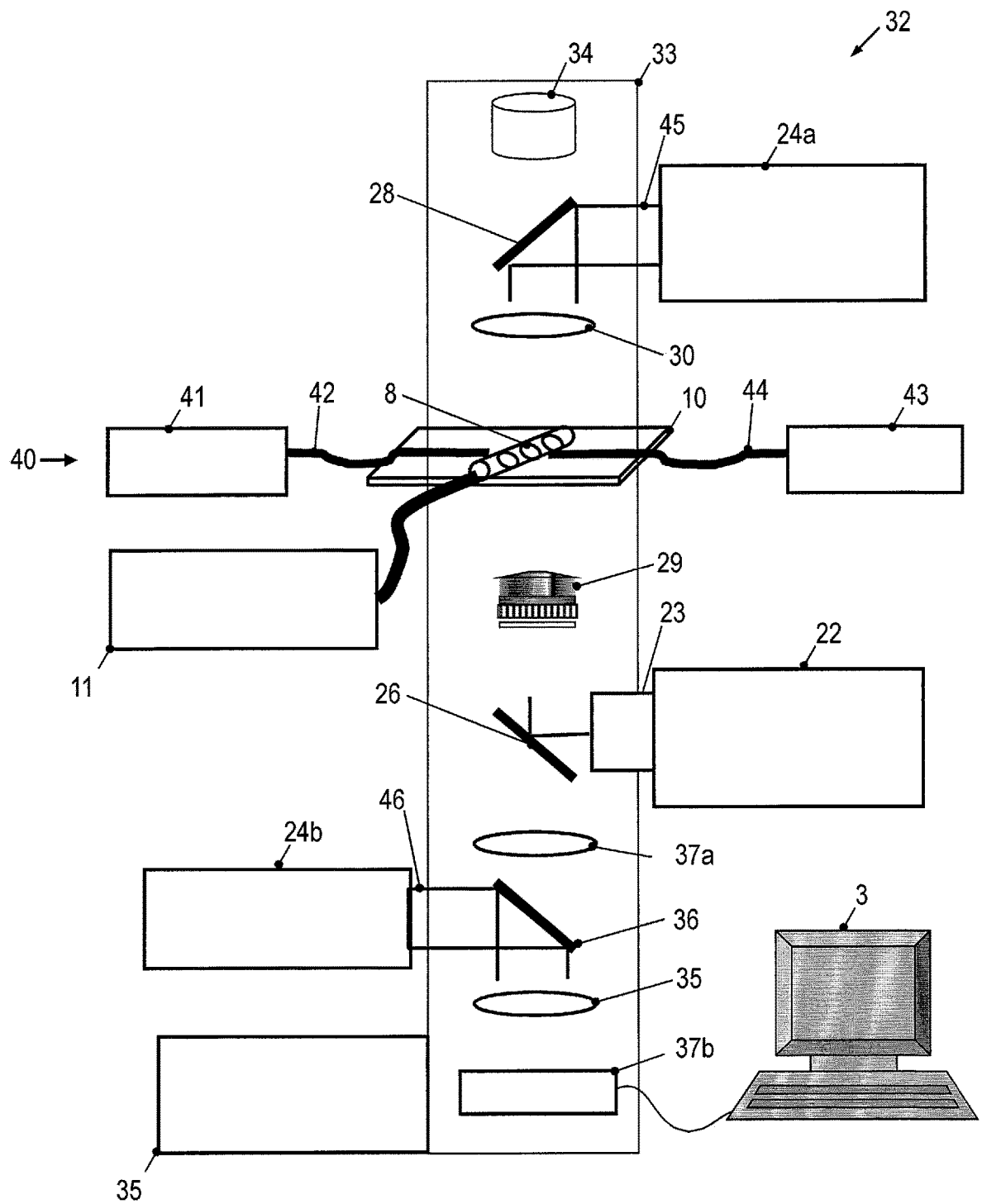
FIG. 2 shows a schematic representation of an apparatus for characterizing biological objects according to an embodiment.

FIG. 2 is a schematic representation of an apparatus 32 for characterizing a cell according to another embodiment. Components of the apparatus 32 which correspond in terms of function and/or construction to components of the apparatus 2 are designated with the same reference numerals as in FIG. 1.

The apparatus has components of a conventional microscope in addition to the modules 24a and 24b of the DHMI device which provide an object wave and reference wave for DHMI and in addition to the Raman device 22. The object and reference wave for DHMI data acquisition and the excitation beam for the Raman spectroscopy may be coupled into the beam path of the microscope. The microscope has an illumination device 34. Other components known from microscopy, which are schematically shown at 35, may be provided. A two-dimensional image sensor 36, such as a CCD sensor, may be provided both for image acquisition for the conventional microscopy on the biological objects and for data acquisition in DHMI. Tube lenses 37a, 37b may be provided in a microscope body 33.

The apparatus 32 has both a device 24a, 24b, 38 for DHMI data acquisition and a device 22 for capturing a Raman spectrum. An object beam 45 for DHMI is coupled into the beam path of the microscope via the beam splitter and is directed onto a fluid channel of a microfluidic system 11 (only schematically shown) via the condenser lens 30. A biological object 8 such as a cell is positioned in the fluid channel for characterization. A reference beam 46 for DHMI is directed onto the image sensor 38 via a beam splitter 36 and a tube lens 37b. An excitation beam for Raman spectroscopy is coupled into the beam path of the microscope via a controllable deflection device 23 and a beam splitter 26. The excitation beam is focussed onto the biological object 8 via the objective 29. The controllable deflection device 23 allows Raman spectra to be detected in a spatially resolved manner on a biological object, e.g. on a cell. Optionally, a scanning over objects on various locations may be provided to detect Raman spectral lines of objects in a time-sequential manner. Light scattered on the object is guided to a spectrometer. For example, the scattered light may be guided via the beam splitter 26 to a Raman spectrometer which is provided in the Raman device 22.

The apparatus 32 has a device 40 for applying a stimulus to a biological object 8. The device comprises two fibres 42, 44 with which an optical signal having a high intensity may be guided to a measurement region of the fluid channel in which the biological object is positioned for performing the measurement. The fibres 42, 44 are coupled to one or plural sources 41, 43 for the optical signal. A laser 41 may be provided, with the laser beam being coupled into the first fibre 42 via suitable optical components and being coupled into the second fibre 44 via optical components 43. The optical fibres 42, 44 may be arranged such that beams which exit from their ends are essentially counter-propagating. Thereby the stimulus may be applied to the biological object 8 by optical means. The stimulus may be applied by a short laser pulse with a Raman spectrum and a DHMI image of the object 8 being captured before application of the laser pulse and/or during the laser pulse and/or after termination of the laser pulse. The stimulus may also be applied over a longer time period to induce a longer lasting deformation of the object 8, for example. A Raman spectrum and a DHMI image of the object 8 may be detected while light is irradiated from the ends of the fibres 42, 44 onto the object. The optical stimulus may also be applied in that a pulsating force is applied onto the biological object which causes resonance vibrations of the biological object. Corresponding data acquisitions may also be performed before the stimulus is applied or when the irradiation of light from the ends of the fibres 42, 44 was terminated.

The object 8 may be characterized based on the Raman spectrum and the DHMI data which are captured before application of the stimulus and which are captured during or after application of the stimulus. For this purpose, a comparison with a data base may be made for example to determine a cell type or a stage of a cell cycle. If no matching entry can be determined for the captured data, the data base may be extended by an entry in which the characteristic properties of the measured Raman spectrum and the information on volume and shape of the object 8 which are reconstructed from the DHMI data are assigned to an object type. In this manner the data base for automatic characterization may be created and extended, respectively.

Figure 3:
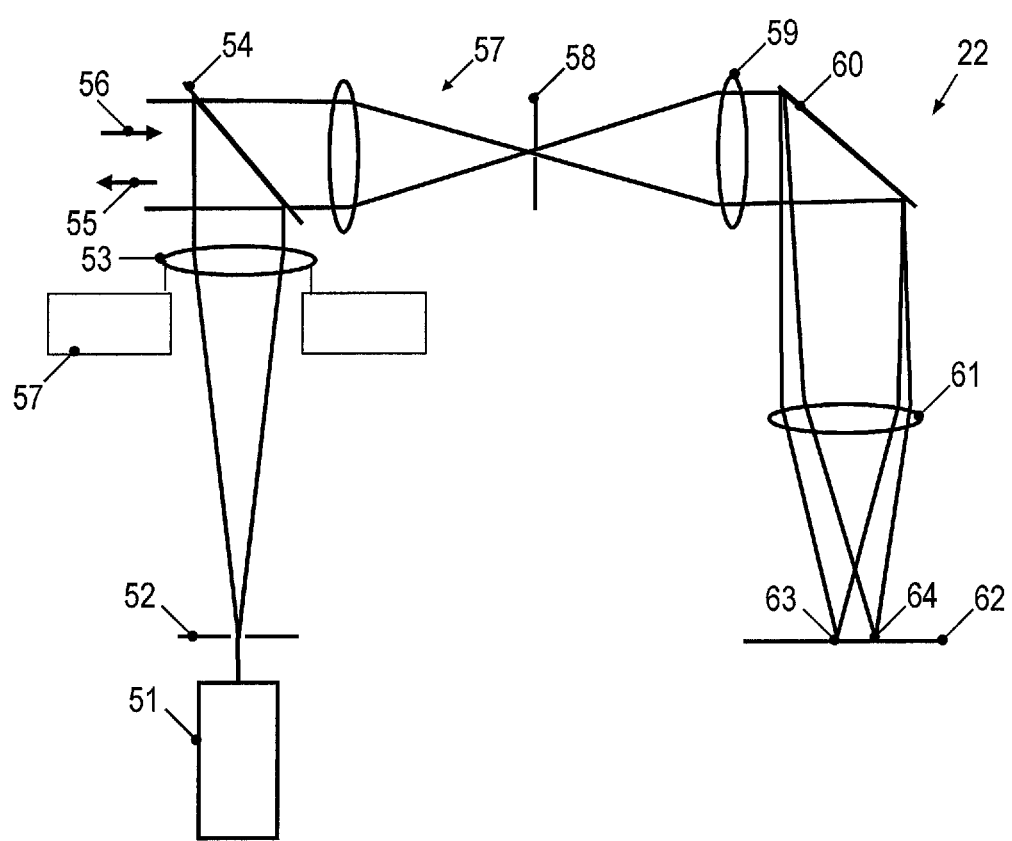
FIG. 3 shows a schematic representation of a device for Raman spectroscopy for an apparatus according to an embodiment.

FIG. 3 is a schematic representation of a Raman device which may be used as a device for capturing a Raman spectrum in the apparatuses according to various embodiments.

The Raman device 22 comprises a laser source 51. An output beam of the laser source 51 is directed via an orifice plate 52, a lens 53 and beam splitter 54 to the biological object as an excitation beam 55 for Raman scattering. Scattered light 56 is directed via the beam splitter 54, a Raman edge filter 57 and an orifice plate 58 to a Raman spectrometer. The Raman spectrometer comprises a grating 60 and a one-dimensional or a two-dimensional image sensor 62, such as a CCD sensor. Lenses 59 and 61 are provided between the orifice plate 38 and the grating 60 as well as between the grating 60 and the image sensor 62, respectively. The scattered light which is separated into its spectral components by the grating 60 is thereby directed onto different positions 63, 64 on the image sensor 62 and is advantageously focussed thereon. The different spectral lines of the Raman spectrum are thus captured on the image sensor 62. When scanning the excitation beam 55 over various points of the object surface plural Raman spectra which are associated with different points or areas on the object surface may be detected in a time-sequential manner.

The Raman device 22 may be configured such that a position of a focus of the excitation beam 55 may be controllably moved in all three spatial directions. The Raman device 22 may be configured such that the position of the focus of the excitation beam 55 for the Raman spectroscopy may be controlled independently of a focus of the beam path of an optical microscope of the apparatus in which the Raman device 22 is used. For this purpose there may be provided a positioning device 57, for example, which is coupled to the lens 53 to displace the same in three orthogonal directions (x, y, z). The position of the focus of the excitation beam 55 may thereby be controlled.

Figure 4:
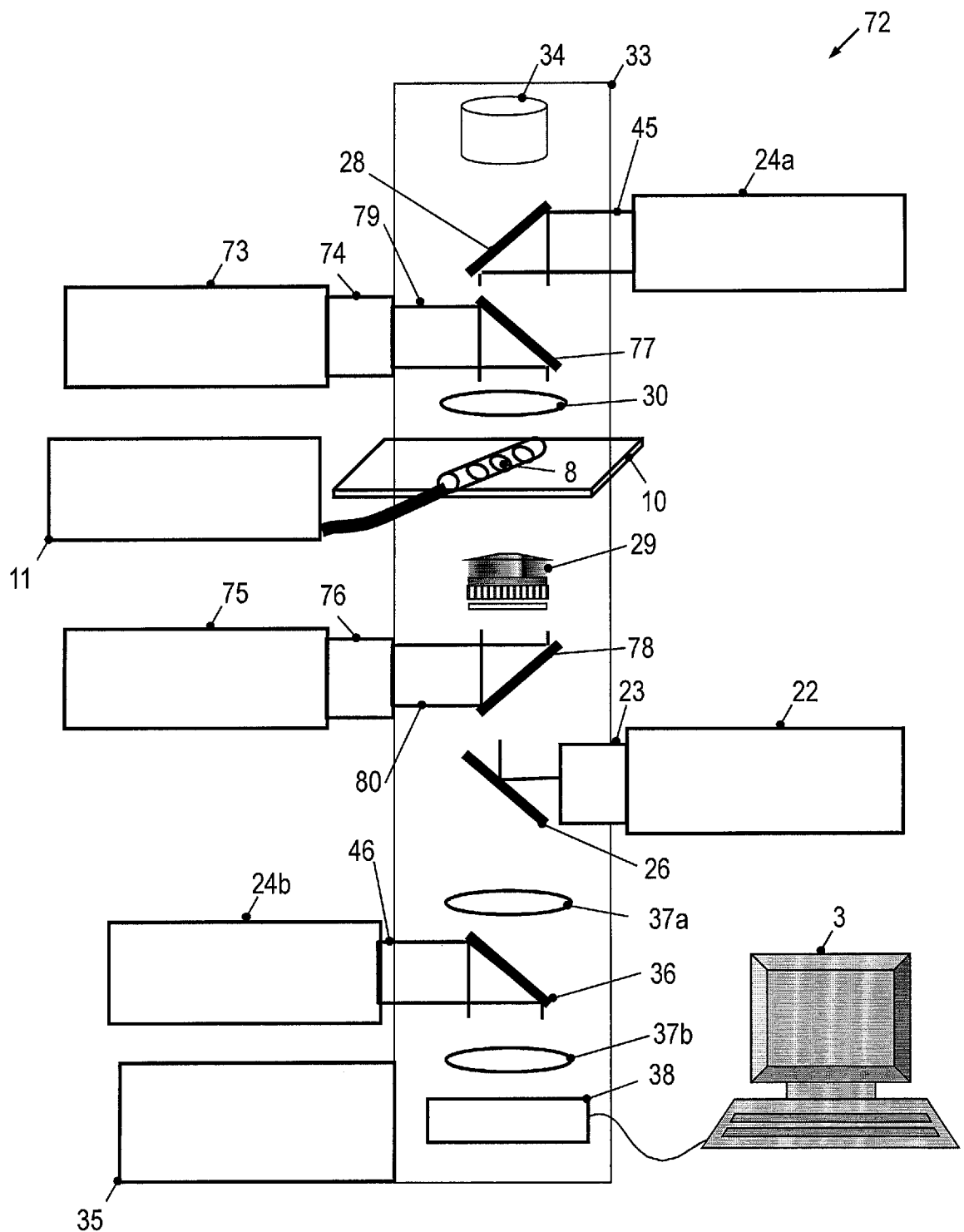
FIG. 4 shows a schematic representation of an apparatus for characterizing biological objects according to another embodiment.

FIG. 4 is a schematic representation of an apparatus 72 for characterizing a cell according to another embodiment. Components of the apparatus 72 which correspond in terms of function and/or construction to components of the apparatus 2 of FIG. 1 or to components of the apparatus 32 of FIG. 2 are designated with the same reference numerals as in FIG. 1 and FIG. 2, respectively.

In the apparatus 72 a stimulus onto a biological object is generated using optical radiation. In this case one dispenses of optical fibres for guiding the laser light up to a measurement region. The device for generating a stimulus has a component 73 which outputs a laser beam 79 to a controllable deflection device 74. The laser beam is directed to a condenser lens 30 via the deflection device 74 and a beam splitter 77. The device for generating a stimulus has a component 75 which outputs a further laser beam 80 to a controllable deflection device 76. The further laser beam 80 is directed to the objective 29 via the deflection device 76 and a beam splitter 78. The components 73, 75 may be ends of optical fibres, for example, using which laser light is guided from a laser to the deflection devices 74, 76. Alternatively, the laser beam may be guided to the deflection devices 74, 76 via suitable deflection mirrors 73, 75. The controllable deflection device 74, 76 may comprise an adjustable element, such as a deflection mirror which is adjustable using a motor, or an electro-optical component, such as a spatial light modulator (SLM). The deflection devices 74, 76 allow the laser beams 79, 80 to be scanned over different positions. In this manner stimuli may be applied to plural biological objects, for example, such as plural cells which are positioned along the longitudinal axis of a fluid channel or in different fluid channels of the microfluidic system. This has the effect that plural biological objects may be characterized in parallel.

The power and the profile of the laser beams 79 and 80 may be set such that a deformation of the biological object 8 is induced. In an implementation the power and the profile of the laser beams 79 and 80 are set such that they exert forces onto the biological object such that the object is compressed in the propagation direction of the beams 79 and 80, i.e. in a vertical direction in FIG. 6. In another implementation the power and the profile of the laser beams 79 and 80 may be set such that they exert forces onto the biological object such that the object is stretched in the propagation direction of the beams 79 and 80, i.e. in a vertical direction in FIG. 6.

The deflection devices 74, 76 are controlled such that the laser beams 79 and 80 are synchronously scanned over various positions. In this manner the stimuli known in the art, such as deformation by compression or stretching along the propagation direction of the counter-propagating beams 79 and 80 may be realized also with scanning over plural positions. The scanning of the excitation beam of the Raman device 22 may advantageously also change between the different measurement regions at the same rate as the beams 79, 80 for applying the stimulus. It is however not required that the excitation beam of the Raman device 22 impinges onto a biological object to be characterized simultaneously with the beams 79, 80.

An implementation of the apparatus for characterizing biological objects in which the laser beams are not guided using optical fibres up to the fluid channel allows a simple and fast scanning of the laser beams. The construction of the apparatus may be simplified.

While deflection devices 74, 76 are shown in FIG. 4, the deflection devices 74, 76 may also be omitted in other embodiments.

Figure 5:
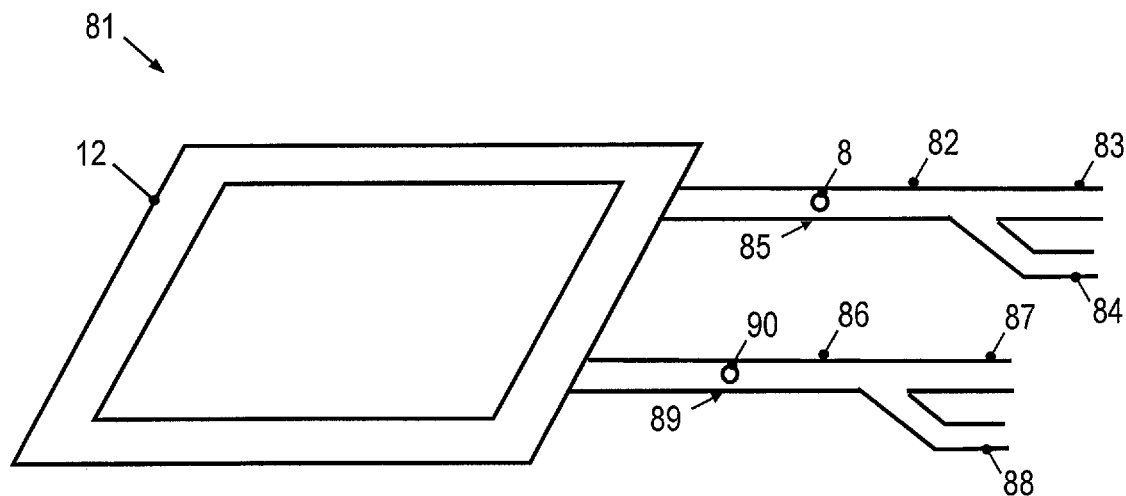
FIG. 5 shows a schematic representation of a microfluidic system for performing measurements in parallel in apparatuses according to an embodiment.

FIG. 5 is a schematic representation of a microfluidic system 81 in which measurements may be performed in parallel in plural fluid channels. A microfluidic system having the configuration shown in FIG. 5 may for example be used when the beams for applying the stimulus or the excitation beam for the Raman spectroscopy can be scanned.

The microfluidic system 81 has a closed loop 12 and plural fluid channels 82, 86 in which measurements may be performed on biological objects. A biological object 8 which is located in a measurement region 85 in the fluid channel 82 during data acquisition for characterization may be selectively sorted into one of plural output channels 83, 84 depending on a result of the characterization. Similarly, a biological object 90 which is located in a measurement region 89 in the fluid channel 86 during data acquisition for characterization may be selectively sorted into one of plural output channels 87, 88 depending on a result of the characterization.

When optical radiation which is used for applying the stimulus and/or for measuring a response to the stimulus is scanned between the measurement regions 85 and 89 in the different fluid channels a characterization of biological objects may be performed in parallel in the two fluid channels 82 and 86.

Figure 6:
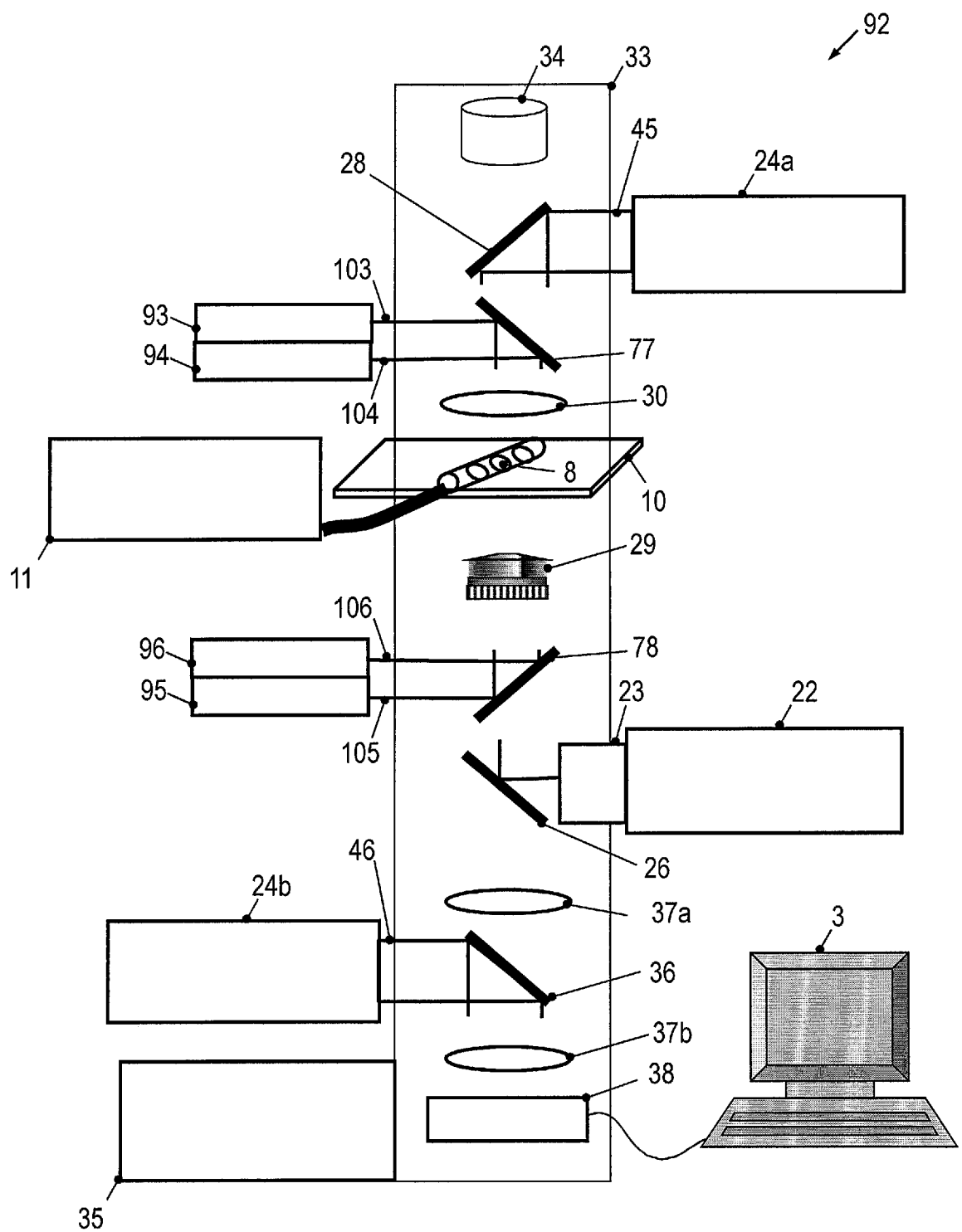
FIG. 6 shows a schematic representation of an apparatus for characterizing biological objects according to another embodiment.

FIG. 6 is a schematic representation of an apparatus 92 for characterizing a cell according to another embodiment. Components of the apparatus 92 which correspond with respect to their function and/or construction to components of the apparatus 2 of FIG. 1, to component of the apparatus 32 of FIG. 2 or to components of the apparatus 72 of FIG. 4 are designated with the same reference numerals as in FIG. 1, FIG. 2 and FIG. 4, respectively.

In the apparatus 92, a stimulus onto a biological object is generated using optical radiation. Similarly to the apparatus 72 of FIG. 4 laser beams are irradiated via the lens 30 or the objective 29, respectively, onto the biological object 8 for applying the stimulus. The device for generating a stimulus has a component 93 which outputs a laser beam 103 which is directed to the lens 30 via a beam splitter 77. A further component 95 is provided which outputs a laser beam 105 which is directed to the objective 80 via a beam splitter 78. Here, the components 93, 95 are configured such that the laser beams 103 and 106 act as a first optical tweezer for a biological object 8. The device for generating the stimulus also has components 94, 96 with which a second optical tweezer for the same biological object 8 is generated. The component 94 outputs a laser beam 104 which is directed to the lens 30 via the beam splitter 77. The component 96 outputs a laser beam 106 which is directed to the objective 29 via the beam splitter 78. The various components 93-96 may be fed from the same laser light source.

The device for generating the stimulus can be configured such that the optical tweezer generated by the laser beams 103 and 105 and the further optical tweezer generated by the laser beams 104 and 106 have a distance which is approximately equal to a diameter of the biological object or can be adjusted to have such a distance. In this manner forces which give rise to a stretching of the biological object may be applied to the biological object.

Figure 7:
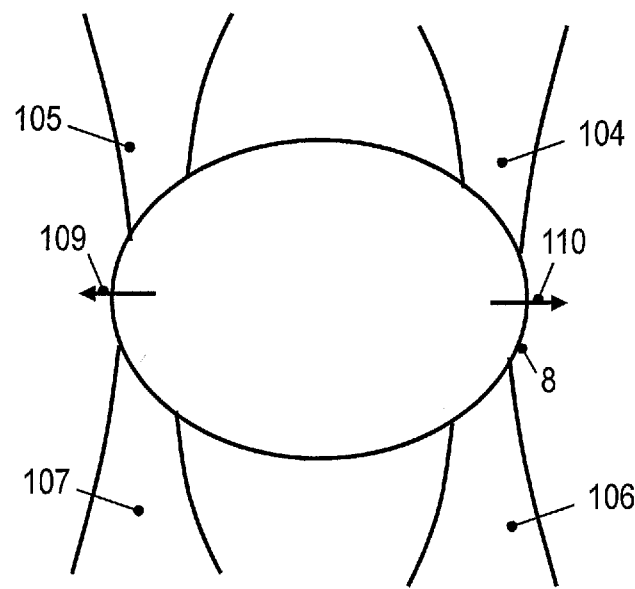
FIG. 7 shows a schematic representation of a cell for explaining the operation of the apparatus of FIG. 6.

FIG. 7 exemplarily shows this action of a pair of optical tweezers. The focal areas of the pair of laser beams 105, 107 and of the pair of laser beams 104, 106 are spaced from each other. Cell portions are drawn into the volume areas having maximum light energy due to the dipole trap effect. If both optical tweezers are set to a suitable distance, for example by a lateral movement of the tweezers away from each other, a stretching of the biological object may be induced as illustrated with arrows 109 and 110.

The apparatus 92 may also be provided with deflection devices (not shown in FIG. 6) to allow one of the pairs 103, 105 or 104, 106 of laser beams or both pairs of laser beams to be adjusted. By adjusting at least one of the pairs of laser beams which form an optical tweezer the apparatus 92 is configurable such that it can induce a change in shape also on biological objects which have clearly different dimensions. The rate at which biological objects can be characterized may be increased by a combined scanning of both optical tweezers.

While embodiments have been described in which a transmission light configuration is used for DHMI data acquisition, a reflection light configuration may also be used in each one of the embodiments.

Figure 8:
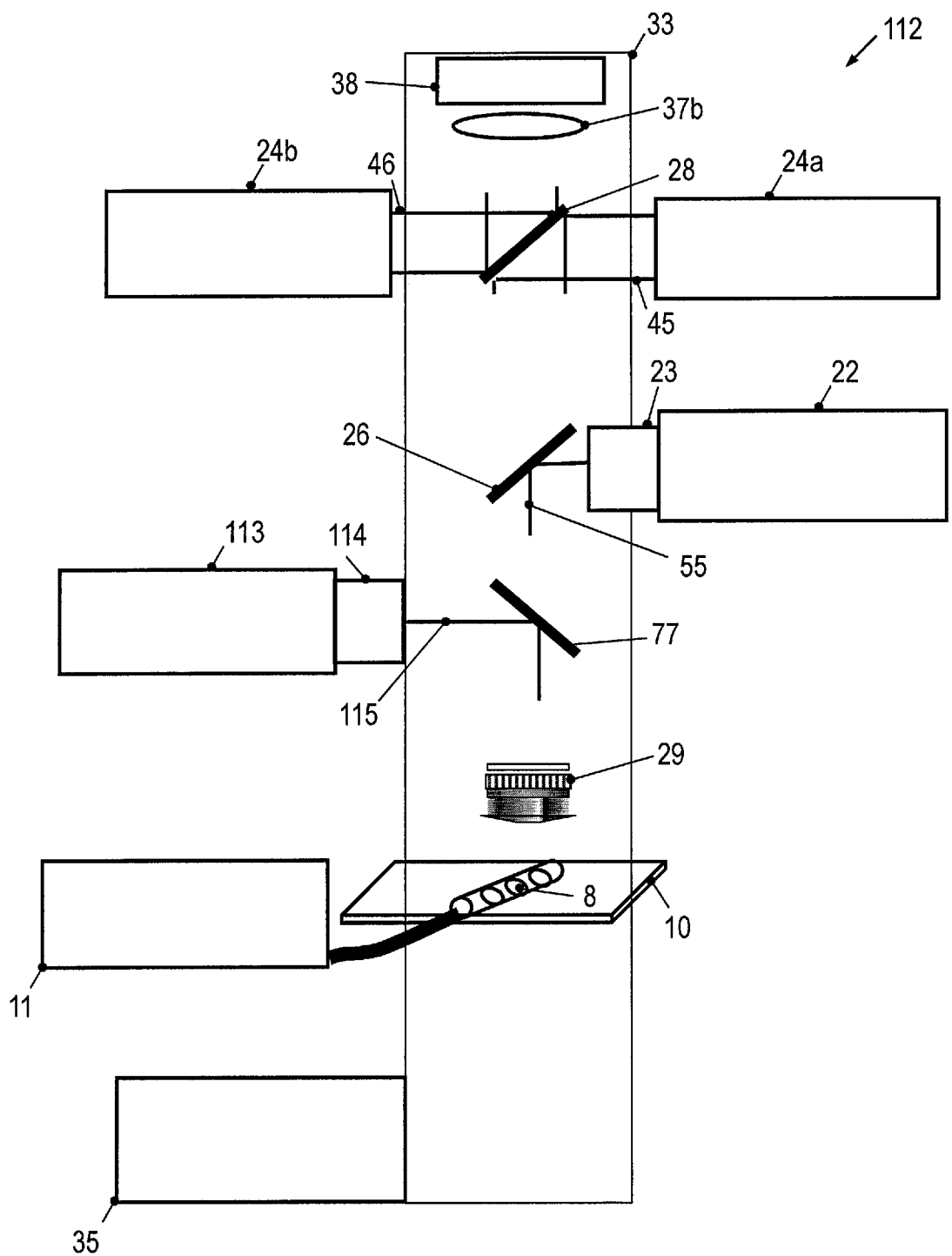
FIG. 8 shows a schematic representation of an apparatus for characterizing biological objects according to another embodiment.

FIG. 8 is a schematic representation of an apparatus 112 for characterizing a cell according to another embodiment. Components of the apparatus 112 which correspond with respect to their function and/or construction to components of the apparatus 2 of FIG. 1, to components of the apparatus 32 of FIG. 2, to components of the apparatus 72 of FIG. 4 or to components of the apparatus 92 of FIG. 6 are designated with the same reference numerals as in FIG. 1, FIG. 2, FIG. 4 and FIG. 6, respectively.

The apparatus 112 has a device for DHMI data acquisition having a source 24a for the object wave 45 and a source 24b for the reference wave 46. The interference pattern resulting from the superposition is captured on the two-dimensional image sensor 38. The apparatus 112 further has a device 22 for performing the Raman spectroscopy. The apparatus 112 has a device 113 for generating a laser pulse or plural laser pulses. A controllable deflection device 114 may optionally be provided such that the laser pulse or the laser pulses may selectively be directed onto one of plural different biological objects or onto different portions of a biological object. Using the micro beam generated by the device 113 a local disturbance on the cell membrane and/or in the cytoplasm of a cell may be generated, for example. The response of the cell to the disturbance may be detected for characterizing the cell. As described with reference to FIGS. 1-7 a DHMI data acquisition and a Raman spectroscopy may be performed to this end before the disturbance was created. A further DHMI data acquisition and a further Raman spectroscopy are performed while the disturbance is being generated or after the disturbance was generated.

Changes in intrinsic properties of biological objects in response to a stimulus may be monitored using the apparatuses. The biological object may be characterized depending on the change in the intrinsic properties. Since the application of the stimulus and the observation can be performed in a destruction-free manner the biological object may be characterized without destruction and may subsequently be subjected to a further manipulation or use.

Figure 9:
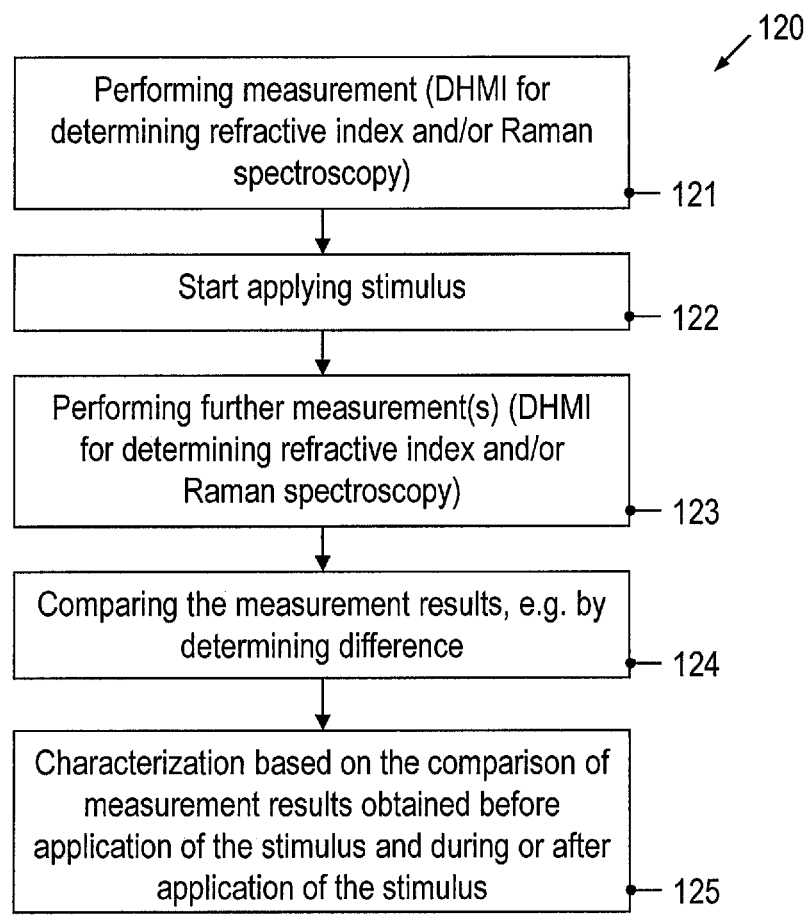
FIG. 9 is a flow diagram representation of a method according to an embodiment.

FIG. 9 is a flow diagram representation of a method 120 according to an embodiment. The method may be performed using the apparatus or the system according to any one of the embodiments described with reference to FIGS. 1-8.

In step 121 a measurement is performed on a biological object. In this step, a DHMI measurement for determining a refractive index is performed and/or a Raman spectrum is captured. The measurement at 121 is performed before application of a stimulus.

In step 122 a stimulus is applied. For applying the stimulus different techniques may be used which were already described and which may include the use of laser light, electromagnetic alternating fields, electromagnetic radiation, ultrasound or similar, for example.

In step 123 at least one further measurement may be performed during or after application of the stimulus on the same biological object on which the measurement was performed in step 121. In this step, a further DHMI measurement for determining the refractive index is performed and/or a further Raman spectrum is captured.

In step 124 the measurement results obtained in 121 and 123 are compared. To this end, a difference between the measurement result obtained at 121 and the measurement result obtained at 123 may be computed, for example. If a Raman spectrum was respectively captured at 121 and 123 a difference spectrum may be computed at 124. If more than two measurements were performed on the biological object a correspondingly greater number of measurement results may be compared. For example, plural Raman spectra which were captured during or after application of the stimulus in a time-sequential manner may respectively be compared to a Raman spectrum which was determined on the same biological object before application of the stimulus.

In step 125 the biological object is characterized based on the comparison of measurement results obtained before application of the stimulus and during or after application of the stimulus. For this purpose a difference spectrum which was determined in step 124 may be compared to a reference difference spectrum stored in a data base, for example.

Figure 10:
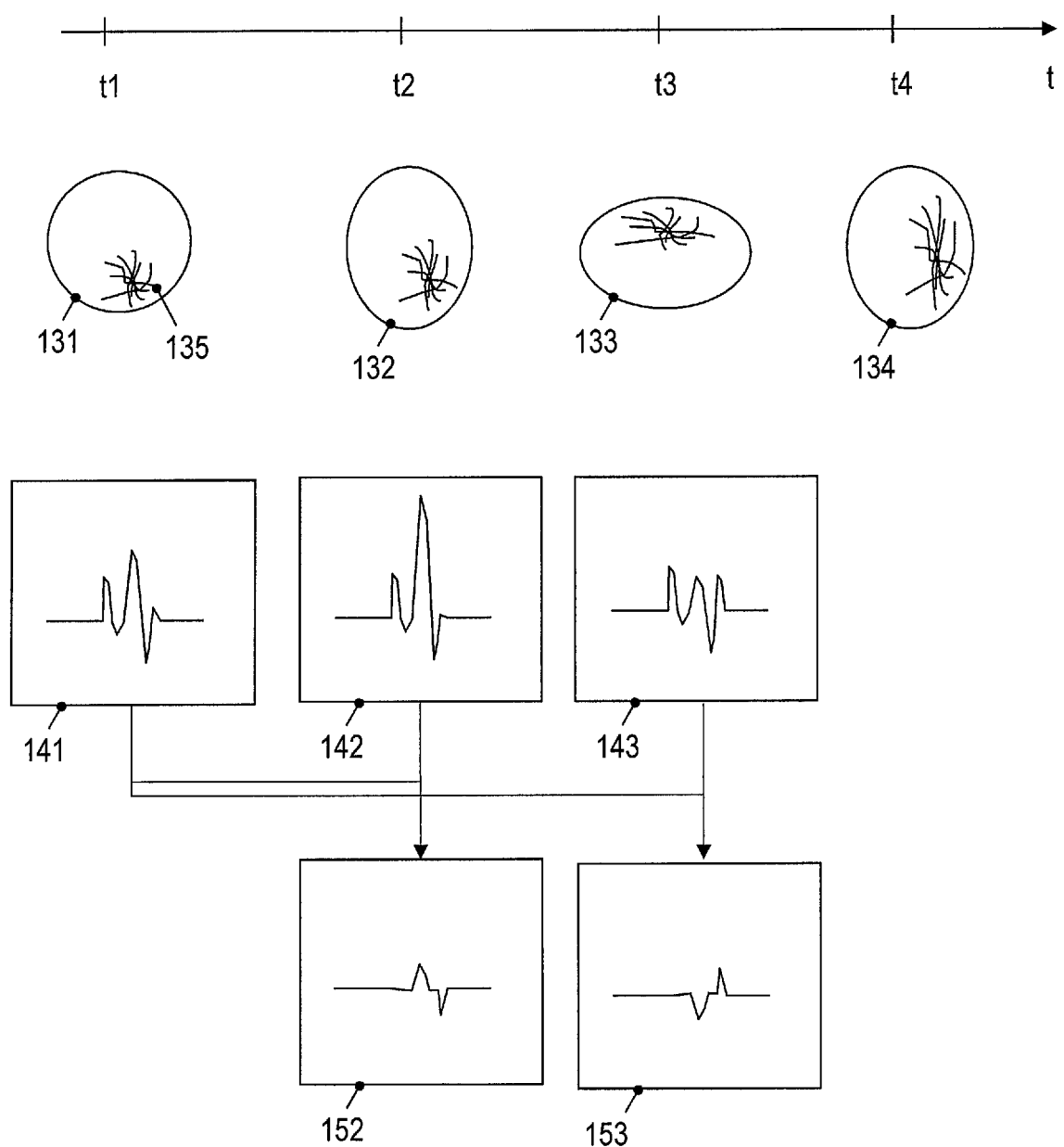
FIG. 10 illustrates a data acquisition and data processing in a method according to an embodiment.

FIG. 10 illustrates the execution of the method according to an embodiment. States 131-134 of a biological object at different times t1, t2, t3 and t4 are shown. Raman spectra 141-143 are detected at times t1, t2 and t3. A difference spectrum 152 between the Raman spectrum 142 detected at t2 and the Raman spectrum 141 detected t1 may be determined from the Raman spectra 141 and 142. A difference spectrum 153 between the Raman spectrum 143 detected at t3 and the Raman spectrum 141 detected at t1 may be determined from the Raman spectra 141 and 143.

As schematically shown the biological object may be stimulated such that it is made to vibrate. At time t1 the biological object, e.g. a cell, has a state 131. With a Raman spectroscopy performed at time t1 information on intrinsic properties of the biological object cell may be obtained, such as information on a density, amount or a type of certain molecules 135 in a.

A pulsating force may be applied to the biological object to excite the biological object to vibrate. A stimulus is applied to the biological object by exciting a vibration, in particular by exciting a resonance vibration. For this purpose an excitation beam of the Raman spectrometer may be irradiated onto the biological object in a pulsed manner with a repetition rate, for example. The repetition rate may be varied until a resonance is reached.

States of the biological object at different times t2, t3 and t4 of the vibration cycle are shown at 132-134. A deformation vibration is shown for illustration. A change in the interior of the biological object is induced by the vibration which can occur in addition to a change in volume and/or shape of the biological object. For example, a density and/or arrangement of the molecules 135 in the interior of the cell may change as a function of time. It is also possible that a type of the molecules 135 in the interior of the cell changes. Such changes lead to a shift of spectral lines and/or to a change in spectral weights of the Raman spectra 142, 143 captured during the vibration at t2 and t3 compared to the Raman spectrum 141 captured at t1. Alternatively or additionally excitation beams having different polarizations may be used in the Raman spectroscopy which is performed at different times.

While embodiments have been described with reference to the drawings modifications may be implemented in other embodiments. While apparatuses have been described in detail in which both a DHMI data acquisition and a Raman spectroscopy are performed to determine a response of a biological object to a stimulus, in other embodiments performing the DHMI data acquisition or performing the Raman spectroscopy may be omitted. For example, in further applications it may be sufficient to characterize the biological object with regard to the change in its Raman spectrum in response to the stimulus. In this case the Raman spectroscopy may provide all data required for characterization.

While embodiments have been described in which the characterization of biological objects after a data base comparison is used for a further action such as for sorting the biological objects, in other embodiments the characterization using the methods and apparatuses described herein may also be used to generate a data base for the automatic sorting or to gain information on the structure of biological objects.

While embodiments have been described in which various optical signals, such as the excitation beam for the Raman spectroscopy are scanned over different positions, no scanning is required in other embodiments.

While embodiments have been described in which a stimulus was generated using optical radiation, in other embodiments the stimulus may also be generated in other ways, for example by ultrasound, high-frequency pulse, electromagnetic radiation or administration of active substances and drugs, respectively. The stimulus may also be generated by the interplay of optical radiation and fluid flow. For example shear forces which are applied by a fluid flow onto an object which is trapped in an optical tweezer may induce deformation of the object. A data acquisition using DHMI and/or Raman spectroscopy may be detected in response to different stimuli. Additionally or alternatively, the response to the irradiation of ultrasound or of an electric or magnetic high-frequency field may be determined.

The invention claimed is:

1. An apparatus for characterizing a biological object, comprising
a holding device adapted to hold a biological object;
a stimulus application device for generating a stimulus on the biological object without contacting the biological object, wherein the stimulus application device is adapted to apply the stimulus to the biological object held by the holding device;
a device for inducing Raman scattering from the biological object when held by the holding device;
a measurement device that detects the Raman scattering and acquires data from measuring the Raman scattering prior to application of the stimulus to the biological object and during or after the application of the stimulus to the biological object;
wherein the measurement device is further configured for data acquisition by means of Digital Holographic Micro Interferometry (DHMI);
wherein the measurement device is configured for ascertaining a response of the biological object to the stimulus;
wherein the measurement device is configured to perform a DHMI-measurement for determining a refractive index and a detection of the Raman scattering before application of the stimulus; and
wherein the measurement device is configured to perform a further DHMI-measurement for determining a further refractive index and a further detection of the Raman scattering after or during the application of the stimulus; and
an evaluation logic configured to compare results of the measurement of the Raman scattering performed before application of the stimulus and results of the further measurement performed during or after the application of the stimulus; said evaluation logic characterizing the biological object as a function of a comparison of the results of the measurement and of the further measurement.

2. The apparatus according to claim 1, wherein the holding device holds the biological object in such a way that there is no contact between the biological object and the stimulus during measurement of the Raman scattering before the application of the stimulus and during the further Raman scattering after or during the application of the stimulus.

3. The apparatus according to claim 1, further comprising one of an optical microscope and an image delivery module.

4. The apparatus according to claim 3, wherein the measurement device comprises a Raman device for detecting the Raman scattering on the biological object; and wherein the Raman device controllably moves a focus of an excitation beam of the Raman device in three orthogonal spatial directions independently of a focus of a beam path of the optical microscope.

5. The apparatus according to claim 4, wherein the Raman device comprises:
one or more lenses; and a positioning device coupled to the one or more lenses and configured to controllably move the one or more lenses in the three orthogonal spatial directions in a controllable manner, and to controllably move the focus of the excitation beam of the Raman device in the three orthogonal spatial directions independently of a focus of the optical microscope.

6. The apparatus according to claim 3, wherein the one of the optical microscope and the image delivery module comprises a camera or one or more lenses.

7. The apparatus according to claim 1, wherein the device for inducing Raman scattering is a laser source that provides an excitation beam to induce the Raman scattering.

8. The apparatus according to claim 7, wherein the device for inducing Raman scattering provides the excitation beam in such a way that the excitation beam acts as optical tweezers that hold, position or sort the biological object.

9. The apparatus according to claim 7, wherein the laser source is configured to simultaneously arrest the biological object during acquiring of Raman spectra by the measurement device.

10. The apparatus according to claim 1, wherein the stimulus application device includes one of an optical source that generates the stimulus for the biological object and a generator that generates one of electromagnetic fields and ultrasonic waves.

11. The apparatus according to claim 1, wherein the measurement device comprises a Raman device for detecting the Raman scattering on the biological object and a DHMI device for capturing a DHMI image of the biological object.

12. The apparatus according to claim 1, further comprising:
an electronically controllable beam deflection device configured to scan a laser beam of the apparatus to generate the stimulus or Raman scattering over a plurality of positions.

13. The apparatus according to claim 1, further comprising:
a microfluidic system that upholds or transports or sorts the biological object.

14. The apparatus according to claim 13, further comprising:
an optical trap that holds or transports or sorts the biological object.

15. The apparatus according to claim 13, further comprising:
an optical trap that holds or transports or sorts the biological object without physical contact within the microfluidic device.

16. The apparatus according to claim 13, wherein the microfluidic system comprises a closed fluid loop for transporting biological objects before and after the measurement is performed.

17. The apparatus according to claim 16, wherein the closed fluid loop of the microfluidic system is configured to continuously transport the biological object.

18. The apparatus according to claim 1, wherein the evaluation logic categorizes the biological object by identifying and/or sorting the biological object based on the comparison of the results of the measurement and of the further measurement.

19. The apparatus according to claim 1, wherein the apparatus is configured to hold a plurality of biological objects, to induce Raman scattering from the plurality of biological objects, and to acquire data from measuring the Raman scattering of the plurality of biological objects, and wherein the evaluation logic identifies and sorts the plurality of biological objects based on the comparison of the results of the measurement and of the further measurement.

20. The apparatus according to claim 19, wherein the apparatus is configured to hold a plurality of cells, and wherein the evaluation logic identifies and sorts the plurality of cells into healthy cells and diseased cells.

21. The apparatus according to claim 19, wherein the apparatus is configured to hold a plurality of cells, and wherein the evaluation logic identifies and sorts the plurality of cells into groups of cells at different stages of cell development.

22. The apparatus according to claim 19, wherein the apparatus is configured to hold a plurality of cells, and wherein the evaluation logic identifies and sorts the plurality of cells into stem cells and body cells.

23. The apparatus according to claim 19, wherein the apparatus is configured to hold a plurality of cells, and wherein the evaluation logic identifies and sorts living cells.

24. The apparatus according to claim 19, further comprising collection vessels, and wherein the evaluation logic automatically directs different types of biological objects to different collection vessels after identification and sorting of the plurality of biological objects.

25. The apparatus according to claim 1, wherein the evaluation logic recognizes one or more of different cell types, cell cycles and clones by evaluating the response upon application of the stimulus to the biological object.

26. The apparatus according to claim 1, wherein the measurement device is further configured to detect a change in the morphology of the biological object using DHMI.

* * * * *